US007662920B2

(12) United States Patent
Geiger et al.

(10) Patent No.: US 7,662,920 B2
(45) Date of Patent: Feb. 16, 2010

(54) FLUORESCENT POLYPEPTIDE COMPLEX

(75) Inventors: Albert Geiger, Penzberg (DE); Hans Hornauer, Peissenberg (DE); Alfons Nichtl, Hohenpeissenberg (DE); Peter Sluka, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 115 days.

(21) Appl. No.: 11/538,940

(22) Filed: Oct. 5, 2006

(65) Prior Publication Data

US 2007/0265430 A1 Nov. 15, 2007

Related U.S. Application Data

(63) Continuation of application No. PCT/EP2005/003589, filed on Apr. 6, 2005.

(30) Foreign Application Priority Data

Apr. 8, 2004 (EP) ................................. 04008587

(51) Int. Cl.
*C07K 14/00* (2006.01)
*A61K 38/00* (2006.01)
(52) U.S. Cl. ............................ 530/350; 977/705; 514/2
(58) Field of Classification Search ....................... None
See application file for complete search history.

(56) References Cited

U.S. PATENT DOCUMENTS

| 4,169,137 | A | 9/1979 | Hirschfeld et al. |
| 4,542,104 | A | 9/1985 | Stryer et al. |
| 5,516,635 | A | 5/1996 | Ekins et al. |
| 5,661,040 | A | 8/1997 | Huff et al. |
| 5,891,741 | A | 4/1999 | Siiman et al. |

FOREIGN PATENT DOCUMENTS

| EP | 0821742 B1 | 2/1998 |
| JP | 58222029 | 12/1983 |
| WO | WO 93/03062 | 2/1993 |
| WO | WO 98/36099 | 8/1998 |
| WO | WO 01/96383 A2 | 12/2001 |

OTHER PUBLICATIONS

Rumbeli et al.,"Crosslinking of Phycobiliproteins from the Cyanobacterium Mastigocladus laminosus with Bis-Imidates: Localization of an Intrasubuint and an Intersubunit Crosslink in C-Phycocyanin", Biol. Chem. vol. 368, pp. 1179-1191 Sep. 1987.*
Allen, J. et al., "Finding Prospective Partners in the Library: the Two-Hybrid System and Phage Display Find a Match," TIBS 20, Dec. 1995, 511-516.
Custer, M. et al., "A Biologic Assay for IL-4," Jounal of Immunological Methods, 128(1990) 109-117.
Dent, Al. et al., "The Preparation of Protein-Protein Conjugates," Bioconjugation (1988) 216-363.
Gantt, E., "Phycobilisomes: Light-Harvesting Pigment Complexes," BioScience vol. 25, No. 12, Dec. 1975, 781-788.
Glazer, A. et al., "Fluorescent Tandem Pycobiliprotein Conjugates, Emission Wavelength Shifting by Energy Transfer," Biophys. J., vol. 43, Sep. 1983, 386-386.
Kronick, M. et al., "Immunoassay Techniques with Fluorescent Pycobiliprotein Conjugates," Clin. Chem. 29/9, 1582-1586 (1983).
Ong, L. et al., "Crosslinking of allophycocyanin," Physiol. Veg., 1985, 23(1) 777-787.
Papageorgiou, G. et al., "Effects of Chaotropic Electrolytes on the Structure and Electronic Excitation Coupling of Glutaraldehyde-and Diimido Ester-Cross-Linked Phycobilisomes," Biochimica et Biophysica Acta, 724(1983) 323-332.
Schechter, Y, et al., "Fluorescent labeling of hormone receptors in viable cells: Preparation and properties of highly fluorescent derivatives of epidermal growth factor and insulin," Proc. Natl. Acad. Sci., vol. 75, No. 5, 2135-2319, May 1978.
Siiman, O. et al., "Fluorescent Neoglycoproteins: Antibody-Aminodextran-Phycobiliprotein Conjugates," Bioconjugate Chem. 1999, 10, 1090-1106.
Telford, W. et al., "Cyanobacterial stabilized phycobilisomes as fluorochromes for extracellular antigen detection by flow cytometry," Journal of Immunological Methods, 254(2001) 13-30.
Trinquet, E. et al., "Allophycocyanin 1 as a Near-Infared Fluorescent Tracer: Isolation, Characterization, Chemical Modification, and Use in a Homogeneous Fluorescence Resonance Energy Transfer System," Analytical Biochemistry 296, 232-244 (2001).

(Continued)

*Primary Examiner*—Anand U Desai
(74) *Attorney, Agent, or Firm*—Marilyn Amick; Roche Diagnostics Operations, Inc.

(57) ABSTRACT

The present invention relates to a method of producing a fluorescent polypeptide complex characterized in that an isolated fluorescent polypeptide is inter-molecularly cross-linked with itself or one or more other polypeptides and wherein said complex is of 40 nm to 500 nm in size, it also relates to a complex obtainable by such method, to conjugates comprising such a fluorescent polypeptide complex and to the use of such complex or conjugate.

15 Claims, No Drawings

OTHER PUBLICATIONS

Tijssen, P., Practice and Theory of Enzyme Immunoassays, 11(1990) the whole book especially 43-78, Elsevier, Amsterdam.

Shapiro, H., Practical Flow Cytometry, 3rd Edition, Wiley-Liss, New York, NY (1995) p. 277.

Haughland, R., Handbook of Fluorescent Probes and Research Chemicals, Molecular Probes, Inc., Sixth Edition, Eugene, OR 97402 (1996).

Shapiro, H., "Practical Flow Cytometry", 3rd edition, Wiley-Liss, New York, NY (1995) p. 277.

* cited by examiner

FLUORESCENT POLYPEPTIDE COMPLEX

RELATED APPLICATION

This application is a continuation of PCT/EP2005/003589 filed Apr. 6, 2005 and claims priority to EP 04008587.0 filed Apr. 8, 2004.

FIELD OF THE INVENTION

The present invention relates to a method of producing a fluorescent polypeptide complex characterized in that an isolated fluorescent polypeptide is inter-molecularly cross-linked with itself or one or more other polypeptides and wherein said complex is of 40 nm to 500 nm in size, it also relates to a complex obtainable by such method, to conjugates comprising such a fluorescent polypeptide complex and to the use of such complex or conjugate.

BACKGROUND OF THE INVENTION

Fluorescent dyes are amongst the classes of molecules which are most broadly used and important in the labeling and detection of biomolecules. Such fluorescent dyes or labels may be classified into low molecular weight organic fluorescent dyes on the one hand and into medium to high molecular weight biomolecules, the fluorescent polypeptides or proteins on the other hand.

The sensitivity which may be achieved for example in an immunoassay using a fluorescent dye as a label largely depends on the number and efficacy of fluorescent molecules present on the specific binding partner used in the detection system, e.g. on an antibody used in an immunoassay. It is generally accepted, that there is rather a low optimal density of low molecular weight fluorophores which may be introduced into, for example, an antibody. This is due to the fact that over-labeling causes negative effects like high background staining, quenching of fluorescence and/or reduced binding of the antibody to its antigen.

Many attempts are known in the art which have lead to quite some improvement in fluorescence detection methods. One attempt has focused on the coupling of low molecular weight fluorescent molecules to biopolymers and thereafter coupling the such labeled biopolymers to a member of a biological binding pair, for example to an antibody. U.S. Pat. No. 4,169,137 discloses that primary-amine-containing polyfunctional polymeric backbone reagents, for example polyethyleneimine or poly-L-lysine can be used to provide a biopolymer which is intensively labeled with a low molecular weight fluorescent dye, for example, with fluorescein isothiocyanate, (FITC).

Fluorescent dextran derivatives have been used for increasing fluorescence intensity, and numerous of such fluorescent dextran derivatives are commercially available. See "Handbook of Fluorescent Probes and Research Chemicals, 6th edition, R. P. Haugland, Molecular Probes, Inc., Eugene, Oreg. 97402, (1996). Fluorescent dextran derivatives consist of soluble dextrans (that is, of dextrans with a molecular weight of 10,000, 40,000, 70,000, 500,000, and 2,000,000 Daltons) conjugated with various fluorescent dyes such as fluorescein, dansyl, rhodamine, and Texas Red. The degrees of substitution in these fluorescent dextran derivatives are 1-2 dye molecules per dextrans of 10,000 Daltons, 2-4 dye molecules per dextran of 40,000 Daltons, 3-6 dye molecules per dextran of 70,000 Daltons, about 64 dye molecules per dextran of 500,000 Daltons, and about 134 dye molecules per dextran of 2,000,000 Daltons. Higher degrees of substitution tend to lead to fluorescence quenching and/or to non-specific interactions. Fluorescein isothiocyanate (FITC) derivatives of dextran or of poly-L-lysine with degrees of substitution ranging from 0.003 to 0.020 molecules of FITC per molecule of glucose and from 0.003 to 0.01 molecule of FITC per molecule of lysyl residue are commercially available from sources, such as Sigma Chemical Company.

Another attempt to increase fluorescence intensity used the fluorescent dye rhodamine, see Shechter, Y., et al., Proc. Natl. Acad. Sci., USA 75 (1978) 2135-2139. Higher than usual for fluorescence intensities were obtained for the peptide hormones insulin and epidermal growth factor by covalent attachment of these peptides to alpha-lactalbumin molecules that were highly substituted with rhodamine molecules (i.e., 7:1). This was accomplished while still retaining some binding affinity of each hormone for its receptor (which is one of the basic requirements of any labeling procedure).

Increasing the number of label molecules or particles per target site, however, does not always work. For example, H. M. Shapiro describes one attempt to increase fluorescence signals by Tomas Hirschfeld et al., at Block Engineering, wherein several hundred fluorescein molecules were attached to a synthetic polymer, polyethyleneimine, which was then conjugated with antibody. The method did not work because fluorescence emission from fluorescein molecules was quenched due to the short nearest neighbor distances between fluorophores on the same polymer molecule. See "Practical Flow Cytometry", 3rd edition, H. M. Shapiro, Wiley-Liss, New York, N.Y., 1995, p. 277.

Although it obviously is possible to introduce a large number of low molecular weight fluorescent dyes into a desired conjugate, the biggest disadvantage even nowadays appears to be the fluorescence quenching which occurs if several low molecular fluorescent dye molecules are in too close a neighborhood.

An alternative attempt is to use latex particles which are labeled with low molecular weight fluorescent dye molecules. The advantages of such labeled microspheres are for example described in U.S. Pat. No. 5,516,635. Whereas such particles appear to provide for a better assay sensitivity, most likely due to a reduced fluorescence quenching, such particles in certain embodiments may suffer from disadvantages like difficulties in a reproducible production of such labeled latex particles, problems in stability, some leakage of fluorescent dye out of such particles and unwanted effects caused by the latex itself.

The medium to high molecular weight fluorescent polypeptides or proteins are quite different to the before discussed low molecular weight fluorescent dyes and therefore require different considerations and approaches. Such a fluorescent protein may carry up to about 30 chromophores per molecule. For example, it has been described that phycoerythrin (PE), a member of the phycobiliprotein family, may have as many as 34 associated chromophores. An antibody conjugated to PE may for example be used in a fluorescent plate immunoassay and such assay has been found to be quite sensitive (Custer, M. C., and Lotze, M. T., J. Immunol. Methods 128 (1990) 109-117).

Phycobiliproteins are light-harvesting proteins included in the phycobilisomes anchored in the thylakoid of cyanobacteria and red algae. They collect the visible light energy and channel it to the chlorophyll photosynthetic system. Due to their exceptional photophysical properties they are of great interest in fluorescence detection procedures.

The biliproteins are normally comprised of from 2 to 3 different subunits, where the subunits may range from about 10,000 to about 60,000 Dalton in molecular weight.

As mentioned above, phycobiliproteins will normally be comprised of 2 to 3 different subunits. For example, native APC consists of 6 phycobiliprotein subunits which make up the 104-kDa phycobiliprotein APC.

It is known that native APC dissociates into subunit monomers under most assay conditions (e.g., at a low protein and/or buffer concentration). This instability, e.g., in physiological buffers represents a major disadvantages of native APC.

It has been found, that APC preparations may be stabilized by intra-molecular cross-linking of APC. Cross-linked and stabilized allophycocyanin preparations (herein referred to as XL-APC) were developed by Glazer and Ong to make this dye more suitable for use in immunoassay (Ong, L. J., and Glazer, A. N., Physiol. Veg. 23 (1985) 777-787). Those authors took a standard preparation of APC and treated it with a chemical cross-linking agent, 1-ethyl-3-(3-dimethylaminopropyl)carbodiimide (EDAC/EDC), such that an average of one alpha subunit was linked to one beta subunit in a covalent manner. The product was then denatured with 8 M urea to dissociate it into its component part: alpha and beta monomeric subunits and covalently linked alpha-beta dimeric subunits. The covalently-linked dimers were separated from the monomers using denaturing gel filtration, and then the dimers were placed in an environment that allowed them to re-associate into an $(\alpha\beta)_3$ complex that displayed unusually high stability compared to native APC. The resultant material is referred to herein as XL-APC. This material has increased stability in the presence of chaotropic salts (such as sodium perchlorate) or at low concentration of buffer compared to native APC. When ran on a denaturing gel, most of the material runs as a single band that is the covalently linked $\alpha\beta$ dimer. It is known that the higher the percentage of cross-linked $\alpha\beta$ dimeric subunits, the better the utility of the XL-APC. A number of XL-APC preparations are commercially available that have various percentages of covalently stabilized $\alpha\beta$ dimer all with greater than 50% of dimer in the final product.

Recently it has been shown (WO 01/96383) that a high fluorescent intensity APC may be obtained if the purification of such APC is performed under conditions avoiding the exposure of the biliproteins to strongly chaotropic agents. Such high fluorescent intensity cross-linked APC is reported to be about 28% more effective in terms of fluorescence quantum yield as compared to an APC as obtained by the methods previously applied. This APC (termed APC1) retains the same $(\alpha\beta)_3$ trimeric structure as APC but incorporates a 10-kDa peptide linker in the core of the molecule. As for a standard APC it is also necessary to cross-link APC1 in order to produce a label of sufficient stability under routine assay conditions.

U.S. Pat. No. 5,891,741 discloses that it is possible to use aminodextran with a special activation characteristic to introduce up to about 20 PE molecules into such aminodextran. When labeled to an antibody of interest such PE-aminodextran leads to an increase in assay sensitivity in the range of about 2.2 to 5.6-fold. This increase in sensitivity goes to the expense of using aminodextran and therefore may also be subject to interferences caused by this carrier reagent. It also appears that for certain application the sensitivity as achieved by such method is not quite sufficient.

An alternative approach to overcome the problems encountered with respect to assay-sensitivity using purified phycobiliproteins has been the use of so-called phycobilisomes as described in EP 821 742. Phycobilisomes are complexes of phycobiliproteins and colorless polypeptides which function as the major light harvesting antennae in blue-green and red algae (Gantt, E., BioScience 25 (1975) 781-788). The major criterion for the functional integrity of these complexes is the demonstration that they exhibit highly efficient transfer of energy between component phycobiliproteins, for example, in Porphyridium cruentum phycobilisomes from phycoerythrin (PE) to phycocyanin (PC) and finally to allophycocyanin (APC). The colorless polypeptides are involved in the assembly and positioning of the phycobiliproteins within the phycobilisomes for proper stability and energy transfer.

Phycobilisomes from different organisms share a number of common properties, including: (1) extremely high "complex molecular weights" ($5\text{-}20\times10^6$ Daltons) i.e., the weight of one mole of a phycobilisome complex comprised of multiple molecules; (2) multiple absorption maxima in the visible range of the electromagnetic spectrum; (3) high molar absorptivities ($e_{max} > 10^7$ M$^{-1}$ cm$^{-1}$); (4) efficient (>90%) directional vibrational energy transfer among constituent phycobiliproteins, commonly from one or more sensitizing species to a terminal acceptor capable of fluorescence; (5) large Stokes shifts relative to isolated phycobiliproteins; (6) high quantum yields of constituent phycobiliproteins; (7) high solubility in aqueous buffers; and (8) allophycocyanin-containing core structures.

Isolated phycobilisomes readily dissociate into free phycobiliproteins and a variety of phycobiliprotein complexes under all but the most favorable conditions. Like for purified APC measures have to be taken to stabilize phycobilisomes, e.g., by intra-molecular cross-linking.

As the skilled artisan will readily appreciate, phycobilisomes are difficult to purify and isolate and even more so to characterize, because of their variation in molecular weight as well as in polypeptide composition.

It therefore was a task of the present invention to provide for a method which when practiced leads to a fluorescent polypeptide complex which at east partially overcomes the above problems.

SUMMARY OF THE INVENTION

It has been found that some of the disadvantages as known in the art can be overcome by a method of producing a fluorescent polypeptide complex characterized in that an isolated fluorescent polypeptide is inter-molecularly cross-linked with itself or one or more other polypeptide to result in a complex that is of 40 nm to 500 nm in size.

The present invention also relates to a fluorescent polypeptide complex comprising an isolated fluorescent polypeptide which is inter-molecularly cross-linked with itself or one or more other polypeptides and which complex is of 40 nm to 500 nm in size.

As the skilled artisan will appreciate, the polypeptide complex of the present invention is spherical. The size of the polypeptide complex given relates to the average size. In further preferred embodiments of the present invention the average size of the polypeptide complex according to the present invention will be in the range of 50 nm to 400 nm, also preferred the average size will be in the range of 55 nm to 350 nm or as well preferred it will be 60 nm or above but below 300 nm.

The present invention further relates to a conjugate comprising the inventive fluorescent polypeptide complex and a partner of a binding pair.

With great advantage the fluorescent polypeptide complex according to the present invention or a conjugate comprising such complex can be used as fluorescent label or in a specific binding assay, respectively. These uses represent further preferred embodiments according to the present invention.

DETAILED DESCRIPTION OF THE INVENTION

As indicated above, in a first and preferred embodiment the present invention relates to a method of producing a fluorescent polypeptide complex characterized in that an isolated fluorescent polypeptide is inter-molecularly cross-linked with itself or one or more other polypeptides and wherein said complex is of 40 nm to 500 nm in size.

The polypeptide part of the fluorescent polypeptide complex according to the present invention preferably consists to at least 30% in weight of the at least one isolated fluorescent polypeptide. More preferred at least 40% in weight of the total polypeptide is the at least one isolated fluorescent polypeptide and most preferred this percentage is 50% in weight or above.

A "fluorescent polypeptide" refers to a fluorescent polypeptide which has a molecular weight in range of 10,000 Dalton to 300,000 Dalton and is capable to emit fluorescent light after appropriate excitation.

The term "isolated" is used to indicate that routine biochemical methods have been used to purify a fluorescent polypeptide, e.g., from natural sources, to a desired homogeneity or purity. The term isolated shall be understood as relating to a content of at least 75% for the desired protein. More preferred the isolated fluorescent polypeptide has a purity of at least 90%, or of at least 95%, respectively.

Preferred fluorescent polypeptides are selected from the groups of fluorescent proteins known as green fluorescent proteins, red fluorescent proteins or phycobiliproteins.

Examples of green fluorescence proteins (GFPs) are Aequorea GFP, Renill GFP, and Phialidium GFP, an example of a red fluorescent protein (RFP) is Discosima RFP, respectively. The fluorescent proteins which are related to a GFP or RFP, for example the cyan fluorescent protein (CFP), or the yellow fluorescent protein (YFP), related to Aequorea GFP, shall be also comprised within GFP or RFP. Preferably GFP and RFP relates to the fluorescent polypeptides specifically mentioned in this paragraph.

Detailed information on the use of GFP can e.g. be found in WO98/36099, wherein a GFP-labeled ligand is used for detection of a target. This labeled ligand comprises a label selected from the group consisting of green fluorescent protein and a fluorescent variant thereof, and a ligand configured to bind to the target. Techniques such as fluorescent microscopy are used to visualize the labeled marker.

The class of the so-called phycobiliproteins (sometimes also referred to as biliproteins) represents a most preferred class of fluorescent polypeptides according to the present invention.

The phycobiliproteins are isolated from a wide variety of algae and cyanobacteria. Many phycobiliproteins are commercially available from various sources including Molecular Probes, Inc., Eugene, Oreg. and Prozyme, Inc., San Leandro, Calif. As the name tells, phycobiliproteins have a polypeptide or protein part, the presence of which provides a wide range of functional groups for conjugation to proteinaceous and non-proteinaceous molecules. Functional groups which are present include amino, thiol, and carboxyl. In some instances, it may be desirable to introduce more functional groups, particularly thiol groups when the phycobiliprotein is to be conjugated to another protein.

Examples of phycobiliproteins useful in the present invention are allophycocyanin, phycocyanin, R-phycoerythrin, allophycocyanin B, phycoerythrocyanin, and B-phycoerythrin. Preferably allophycocyanin is used in a method according to this invention.

As described above, intro-molecular cross-linking is advantageous to stabilize a phycobiliprotein.

The phycobiliprotein comprised of from 2 to 3 different phycobiliprotein subunits may be also referred to as a phycobiliprotein monomer. By way of example the APC monomer consists of 6 phycobiliprotein subunits, whereas the APC1 monomer consists of 6 phycobiliprotein subunits and additionally the 10 kDa linker polypeptide.

Preferably the isolated fluorescent polypeptide used in a method according to the present invention is a phycobiliprotein monomer.

It is also preferred that the phycobiliprotein used to produce the fluorescent polypeptide complex according to the present invention is a phycobiliprotein wherein the $\alpha$ and $\beta$ subunits are covalently linked. Most preferred the fluorescent polypeptide is APC or APC1, wherein $\alpha$ and $\beta$ subunits are linked together within APC or APC1, like in XL-APC or XL-APC1, respectively, each comprising three $\alpha$ and three $\beta$ subunits. The cross-linking in between subunits of a fluorescent protein, e.g., in between the $\alpha$ and $\beta$ subunits of APC as known in the art is an intra-molecular cross-link, which, e.g., is within the APC monomer. On the contrary the cross-linking according to the present invention is between several monomers of a fluorescent polypeptide, like for example XL-APC, resulting in a highly polymeric polypeptide complex, comprising several to many APC monomers.

Alternatively, an isolated fluorescent polypeptide may be cross-linked with one or more other polypeptides. The one or more other polypeptide may be a polypeptide which works as a carrier molecule, for example, it may be bovine serum albumin. Preferably, the one or more other polypeptide is selected from the group consisting of one partner of a binding pair, and/or a second isolated fluorescent polypeptide.

In certain embodiments it will be advantageous if the fluorescent polypeptide complex according to the present invention comprises at least a further fluorescent molecule. Such fluorescent molecule may either be a low molecular weight dye or a further fluorescent protein. Preferably the further fluorescent molecule is a second fluorescent polypeptide. As the skilled artisan will readily appreciate such a second fluorescent polypeptide preferably is selected to provide for sufficient overlap in its emission or absorption spectrum with the absorption or emission spectrum, respectively, of the first fluorescent polypeptide. This way or greater wave-length shift from absorption to emission wave-length can be achieved. The advantages of such wave-length shift are known to the skilled artisan and can e.g. be gathered from WO 93/03062.

Most preferred the one or more other polypeptide is a specific binding agent, e.g., a partner of a specific binding pair.

A specific binding agent has at least an affinity of $10^7$ L/mol for its corresponding target molecule. The specific binding agent preferably has an affinity of $10^8$ L/mol or even more preferred of $10^9$ L/mol for its target molecule. As the skilled artisan will appreciate the term specific frequently is used to additionally indicate that biomolecules other than the target molecule present in a sample do not significantly bind to the specific binding agent. Preferably the level of binding to a biomolecule other than the target molecule results in a binding affinity which is only 10%, more preferably only 5% of the affinity for the target molecule or worse. A most preferred specific binding agent will fulfill both the above preferred criteria for affinity as well as for specificity.

The two members or partners of a specific binding pair are the best known examples of specific binding agents. Well-known and suitable binding pairs in biology, biochemistry or immunochemistry are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, receptor/ligand e.g. steroid hormone receptor/steroid hormone. These binding pairs may also be referred to as bioaffinity binding pairs. Preferred binding pair members are a hapten or an antigen and an antibody binding to this hapten or antigen, respectively.

Also preferred are specific binding agents obtainable by phage display (see e.g., Allen, J. B., et al., TIBS 20 (1995) 511-516).

Preferably, the partner of a binding pair is selected from the group consisting of an antibody and a hapten.

The term antibody refers to a polyclonal antibody, a monoclonal antibody, fragments of such antibodies, as well as to genetic constructs comprising the binding domain of an antibody. Any antibody fragment retaining the above criteria of a specific binding agent can be used.

Antibodies are generated by state of the art procedure, e.g., as described in Tijssen (Tijssen, P., Practice and theory of enzyme immunoassays 11 (1990), the whole book, especially pages 43-78; Elsevier, Amsterdam).

Haptens are small molecules with a molecular weight of less than 2 kDa, preferably less than 1.5 kDa and most preferred less than 1 kDa. A hapten itself is not immunogenic. However, when conjugated to appropriate carrier molecules, such conjugates may be used to render the hapten immunogenic and thus to generate an appropriate immune response. Polyclonal as well as monoclonal antibodies against haptens of various kinds are well-known in the art. Well-known haptens are for example fluorescein, di-nitro-phenyl-phosphate, steroidal hormones, many low molecular weight drugs, digoxin and digoxigenin.

A method of producing the fluorescent polypeptide complex according to the present invention preferably comprises the steps of (a) providing at least one isolated fluorescent polypeptide and optionally a second polypeptide, (b) adding a chemical cross-linking reagent, (c) terminating the reaction once a polypeptide complex of the desired size is obtained, and (d) isolating the complex obtained in steps (b) and (c).

Whereas it is possible to isolate and purify the inter-molecularly cross-linked fluorescent polypeptide complex and thereafter using such purified complex to link it to a biomolecule, for example, to one partner of a binding pair, it is also possible to pre-polymerize the at least one isolated fluorescent polypeptide and optionally at least a second polypeptide and later-on adding to this reaction mixture one binding partner of a binding pair. This method preferably comprises the steps of (a) providing at least one isolated fluorescent polypeptide and optionally a second polypeptide, (b) adding a chemical cross-linking reagent, (c) adding one partner of a binding pair, (d) terminating the reaction once a polypeptide complex of the desired size is obtained, and (e) isolating the complex obtained in steps (b), (c), and (d).

The fluorescent polypeptide complex according to the present invention has a size of 40 to 500 nm. The size given relates to the average size, since, as a skilled artisan will appreciate, there will always be some range, scatter or distribution in size. It is known that the size determination to some extend may depend on the criteria used in assessing size. In order to assess the size of a polypeptide complex according to the present invention the photon correlation spectroscopy (PCS) is used under the following conditions. The sample material is diluted in 1 mM sodium chloride as recommended by the manufacturer of the PCS instrument (Malvern Zetasizer HSa) and the size analysis performed in the automatic mode.

A fluorescent polypeptide complex produced according to the present invention has significant advantages in terms of sensitivity, as compared to state-of-the-art conjugates. This is demonstrated in the Examples given.

The chemical cross-linking reagent and thereby the mode and strategy of the inter-molecular chemical coupling can be selected as required. Coupling chemistries targeting —SH, —$NH_2$ or —$COO^-$ residues as well as the —OH group of tyrosines, the imidazol group of histidines or the heterocyclic imino groups of tryptophanes are at hand. Several appropriate coupling chemistries are known from the art for each of these functional groups (Aslam, M. Dent. A., The preparation of protein-protein conjugates in "Bioconjugation" (1998) 216-363, London, McMillan).

For many applications the sensitivity and stability of a fluorescent polypeptide complex as produced in the above methods is sufficient. However, in some applications long term stability is crucial. It surprisingly has been found that an additional step of cross-linking of the above complex may be quite advantageous in terms of stability. The method according to the present invention therefore preferably in addition comprises the step of adding a further cross-linking reagent once the fluorescent polypeptide complex of 40 to 500 mm in size has been obtained. This way the fluorescent polypeptide complex becomes even more inter-molecularly cross-linked and is further stabilized. Preferred chemical cross-linking reagents in this second cross-linking step are homobifunctional NHS esters, and homobifunctional imidoesters. Most preferably, disuccinimidyl suberate (DSS) or bis(sulfosuccinimidyl)suberate ($BS^3$) are used.

In a preferred embodiment the present invention relates to a conjugate comprising the fluorescent polypeptide complex according to the present invention and a partner of a binding pair. Such conjugate may be obtained by first producing and isolating the fluorescent polypeptide complex and thereafter coupling it to the partner of a binding pair of by "co-polymerizing" at least a fluorescent polypeptide and a partner of a binding pair.

In a further preferred embodiment the present invention relates to the use of a conjugate comprising the fluorescent polypeptide complex according to the present invention and the partner of a biological binding pair in a specific binding assay.

Array test systems wherein several analytes (e.g., polynucleotides or immunologically detectable molecules) are detected in parallel are becoming increasingly important. Detection of an analyte in such an array usually is based on a sandwich assay principle, i.e., an immobilized capture and a directly or indirectly labeled detection reagent. For example, it is possible to attach several antibodies of different specificity to a solid phase and to analyze a sample for the presence, absence or concentration of each of the corresponding analyzes. The antibodies have to be attached to a small area but at a very high density. Labels which allow for detection with a very high sensitivity are of utmost importance in such an array, because only rather a few possibilities for binding of a detection reagent exist. Details relating to the theory of such array test systems can e.g. be found in U.S. Pat. No. 5,516,635.

In a preferred embodiment according to the present invention a conjugate comprising one partner of a binding pair and the fluorescent polypeptide complex according to the present invention is used as a detection reagent in an array test system.

As the skilled artisan will readily appreciate, besides the specifically disclosed application of the novel fluorescent polypeptide complex as a label for a binding partner in an immunoassay a large variety of other different applications exist, wherein the inventive fluorescent polypeptide complex is used as a fluorescent label. In a further preferred embodiment the present invention therefore relates to the use of a complex according to the present invention as a fluorescent label in general. Only to give an example the polypeptide complex according to the present invention may be used in high sensitivity screening procedures, e.g., in the labeling of enzyme substrates and in the screening for and discovery of novel drug.

The following examples and references are provided to aid the understanding of the present invention, the true scope of which is set forth in the appended claims. It is understood that modifications can be made in the procedures set forth without departing from the spirit of the invention.

SPECIFIC EMBODIMENTS

Example 1

SATP Activated of XL-APC

Where not specified otherwise, the reactions were performed at room temperature (RT). 10 mg XL-APC (PB25, Prozyme, San Leandro Calif.) was centrifuged for 10 min at 27000 g and the supernatant was discarded. The pellet was resuspended 1 mL. 50 mM phosphate buffer pH 8.2 and the solution was dialyzed against 50 mM phosphate buffer pH 8.2 over night. XL-APC was reacted in 1:12 molar ratio with N-succinimidyl acetylthiopropionate for 3.5 h at RT. The SATP-activated XL-APC was dialyzed over night at 4° C. against 50 mM phosphate buffer pH 6.6. De-blocking of SH-groups was done by adding 25 µl of 1 M hydroxylamine and incubating for 1 h.

Example 2

MHS Activation of XL-APC 10 mg XL-APC was centrifuged for 10 min at 27000 g and the supernatant was discarded. The pellet was resuspended 1 mL 50 mM phosphate buffer pH 6.7 and the solution was dialyzed against 50 mM phosphate buffer pH 6.7 over night. MHS-activation of XL-APC was done with maleimidohexanoyl-N-hydroxysuccinimide ester at 1:12 molar ratio in phosphate buffer pH 6.7 for 2 h at 4° C. The activated XL-APC was dialyzed over night at 4° C. against 50 mM phosphate buffer pH 6.6.

Example 3

MHS Activation of Anti-DIG Monoclonal Antibody (MAb)

Immunoglobulin (IgG) of an anti-digoxigenin (DIG) MAb was used. 20 mg anti-DIG MAb was dissolved in 1 mL 100 mM phosphate buffer pH 7.0 dialyzed against the same buffer over night. MHS-activation of anti-DIG MAb was done with maleimidohexanoyl-N-hydroxysuccinimide ester at 1:8 molar ratio for 2 h at 4° C. The activated anti-DIG MAb was dialyzed at 4° C. against 50 mM phosphate buffer pH 6.6 over night.

Example 4

Preparation of an XL-APC-Anti-DIG Conjugate 5 mg of de-blocked SATP-activated XL-APC from Example 1 were reacted with 5 mg MHS-activated anti-DIG MAb from Example 3 in phosphate buffer pH 7.0 for 2 h at RT. The reaction was quenched by adding 15 µL of 100 mM cysteine solution and incubating for 15 min. Finally, 100 µL 0.5 M jodoacetamide was added and incubated for 30 min at RT. The reaction mix was dialyzed against 50 mM phosphate buffer pH 6.6 over night. The crude product was purified on a SUPEROSE 6 column (buffer: 50 mM phosphate pH 6.6, flow rate: 0.5 mL/min). The conjugate was dialyzed against HEPES buffer pH 7.2 at 4° C. over night.

Example 5

Preparation of a Poly(XL-APC)-Anti-DIG Conjugate 4 mg of deblocked SATP-activated XL-APC from Example 1 were reacted with 4 mg MHS-activated XL-APC from Example 2 in phosphate buffer pH 6.85 at RT. After 2 h polymerization time 16 mg of MHS-activated anti-DIG MAb from Example 3 wad added and incubated for additional 90 min. The reaction was quenched by adding 15 µL of 100 mM cysteine solution and incubating for 10 min. Finally, 50 µL 0.5 M jodoacetamide was added and incubated for 30 min at RT. The reaction mix was dialyzed against 50 mM phosphate buffer pH 6.6 overnight. The crude product was purified on a SUPEROSE 6 column (buffer: 50 mM phosphate pH 6.6, flow rate: 0.5 mL/min). The conjugate was dialyzed against HEPES buffer pH 7.2 at 4° C. over night.

Example 6

Evaluation of Conjugates

A biotin and digoxigenin labeled protein was immobilized onto a streptavidin coated polystyrene chip. The chip was incubated at a final concentration of 250 µg/mL of the conjugate from Example 4 or 5, respectively, in HEPES buffer. A He/NE laser was used for fluorescence excitation and a CCD camera was used for fluorescence detection.

As can be seen from Table 1, the resulting signal from the poly(XL-APC)-anti-DIG conjugate from Example 5 was about 20 times higher than the signal intensity obtained with the state of the art XL-APC-anti-DIG conjugate from Example 4.

TABLE 1

| Conjugate | Signal intensity |
|---|---|
| (XL-APC)-anti-DIG | 379 |
| Poly(XL-APC)-anti-DIG | 6930 |

Example 7

Preparation of DSS-Cross-Linked-(poly(XL-APC)-anti-DIG) Conjugate

The pH of the conjugate solution from Example 5 was adjusted to pH 8 with phosphate buffer. DSS in DMSO was added in a 20-fold molar excess as compared to the incorporated antibody and incubated for 30 min at RT. To quench the reaction glycine was added at a final concentration of 30 mM. The conjugate was dialyzed against HEPES buffer pH 7.2 at 4° C. over night.

Example 8

Stability Testing of the Conjugate

For stability testing, 250 μM solutions of the conjugates from Examples 5 and 7 were incubated for 14 days at 35° C. Evaluation of the conjugates was performed prior to and after incubation at 35° C. according to the method described in Example 6.

TABLE 2

| Conjugate | Remaining signal intensity (14 d at 35° C. in % of starting signal) |
|---|---|
| Poly(XL-APC)-anti-DIG | 30% |
| DSS-cross-linked-poly(XL-APC)-anti-DIG | >95% |

As can be seen from Table 2, the signal achieved with the second conjugate remains very stable even after storage for two weeks at 35° C.

What is claimed is:

1. A method for producing a fluorescent polypeptide complex comprising the steps of
    providing an isolated fluorescent polypeptide, wherein the isolated fluorescent polypeptide is a phycobiliprotein comprising covalently linked α and β subunits,
    adding a chemical cross-linking reagent to the isolated fluorescent polypeptide whereby crosslinking of the isolated fluorescent polypeptide occurs to form a fluorescent polypeptide complex, wherein the crosslinking is terminated once a fluorescent polypeptide complex of 40 to 500 nm is obtained, and
    isolating the fluorescent polypeptide complex.
2. The method of claim 1, wherein the phycobiliprotein is allophycocyanin.
3. The method of claim 1 wherein an additional polypeptide is also provided and cross-linked with the isolated fluorescent polypeptide.
4. A fluorescent polypeptide complex obtained by the method of claim 1.
5. A conjugate comprising a member of a specific binding pair and a fluorescent polypeptide complex produced by the method of claim 1.
6. The conjugate of claim 5 wherein the member of a specific binding pair is selected from the group consisting of antibodies and haptens.
7. The conjugate of claim 5 wherein the member of a specific binding pair is an antibody to digoxigenin and the fluorescent polypeptide complex comprises allophycocyanin.
8. An isolated fluorescent polypeptide complex comprising a fluorescent polypeptide cross-linked with itself and having a size of 40 to 500 nm.
9. The fluorescent polypeptide complex of claim 8 wherein the fluorescent polypeptide is selected from the group consisting of green fluorescent proteins, red fluorescent proteins, and phycobiliproteins.
10. The fluorescent polypeptide complex of claim 9 wherein the fluorescent polypeptide is allophycocyanin.
11. A method for producing a conjugate comprising a member of a specific binding pair and a fluorescent polypeptide complex, the method comprising the steps of
    providing an isolated fluorescent polypeptide,
    adding a chemical cross-linking reagent to the isolated fluorescent polypeptide whereby the isolated fluorescent polypeptide is cross-linked with itself to form a fluorescent polypeptide complex having a size of 40 to 500 nm,
    adding a member of a specific binding pair to the fluorescent polypeptide complex and chemical cross-linking, reagent whereby a conjugate is formed comprising a member of a specific binding pair and a fluorescent polypeptide complex, and
    isolating the conjugate.
12. The method of claim 11 wherein the isolated fluorescent polypeptide is selected from the group consisting of green fluorescent proteins, red fluorescent proteins, and phycobiliproteins.
13. The method of claim 11 wherein the isolated fluorescent polypeptide is allophycocyanin.
14. The method of claim 11 wherein the member of a specific binding pair is a digoxigenin antibody.
15. A conjugate produced by the method of claim 11.

* * * * *

UNITED STATES PATENT AND TRADEMARK OFFICE
CERTIFICATE OF CORRECTION

PATENT NO. : 7,662,920 B2  Page 1 of 1
APPLICATION NO. : 11/538940
DATED : February 16, 2010
INVENTOR(S) : Geiger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 226 days.

Signed and Sealed this

Thirtieth Day of November, 2010

David J. Kappos
*Director of the United States Patent and Trademark Office*